us005702397A

United States Patent [19]
Goble et al.

[11] Patent Number: 5,702,397
[45] Date of Patent: Dec. 30, 1997

[54] LIGAMENT BONE ANCHOR AND METHOD FOR ITS USE

[75] Inventors: E. Marlowe Goble; David P. Luman; Alan Chervitz, all of Logan; C. Brad Story, Liberty; Ramarao Gundlalpalli, Logan, all of Utah

[73] Assignee: MedicineLodge, Inc., Logan, Utah

[21] Appl. No.: 603,119

[22] Filed: Feb. 20, 1996

[51] Int. Cl.$^6$ .................................................. A61B 17/84
[52] U.S. Cl. .................................. 606/72; 606/73; 606/86
[58] Field of Search ................................ 606/60, 86, 88, 606/72, 73, 75, 232; 623/13

[56] References Cited

U.S. PATENT DOCUMENTS

| | | |
|---|---|---|
| Re. 34,293 | 6/1993 | Goble et al. . |
| 4,301,551 | 11/1981 | Dore et al. . |
| 4,400,833 | 8/1983 | Kurland . |
| 4,467,478 | 8/1984 | Jurgutis . |
| 4,590,428 | 5/1986 | Hunt et al. . |
| 4,597,776 | 7/1986 | Hilal et al. . |
| 4,605,414 | 8/1986 | Czajka . |
| 4,668,233 | 5/1987 | Seedhom et al. . |
| 4,744,793 | 5/1988 | Parr et al. . |
| 4,772,286 | 9/1988 | Goble et al. . |
| 4,773,417 | 9/1988 | Moore et al. . |
| 4,834,752 | 5/1989 | Van Kampen . |
| 4,870,957 | 10/1989 | Goble et al. . |
| 4,927,421 | 5/1990 | Goble et al. . |
| 4,950,270 | 8/1990 | Bowman et al. . |
| 4,997,433 | 3/1991 | Goble et al. . |
| 5,129,902 | 7/1992 | Goble et al. . |
| 5,139,520 | 8/1992 | Rosenberg . |
| 5,147,362 | 9/1992 | Goble . |
| 5,458,601 | 10/1995 | Young, Jr. et al. ................ 606/72 |

Primary Examiner—Michael Buiz
Assistant Examiner—Daphna Shai
Attorney, Agent, or Firm—M. Reid Russell

[57] ABSTRACT

A bone anchor and method for its use in an arthroscopic and open soft tissue surgical procedure to mount a ligament graft, or the like, under tension and at variable lengths in a tunnel section that is formed through a bone or bones. The bone anchor embodiments of the invention each have a body for mounting into and/or adjacent a bone cortex surface in a tunnel section to allow at least one suture or shaft that has been fitted through the bone anchor, and is attached to the ligament graft to be pulled through the bone anchor. The suture or shaft to pass across a movable clamp fitted within the body to move so as to allow the suture or shaft to be pulled freely through the bone anchor distal, but will clamp against the suture or shaft, prohibiting its being pulled back therethrough. A pulling of the suture or shaft through the seated bone anchor applies a tension and sets a required length to a graft whose opposite end is secured, with the clamp locking against a section of that suture or shaft, to maintain that applied tension. Whereafter, the excess suture or shaft can be cut away, permanently mounting the graft.

18 Claims, 13 Drawing Sheets

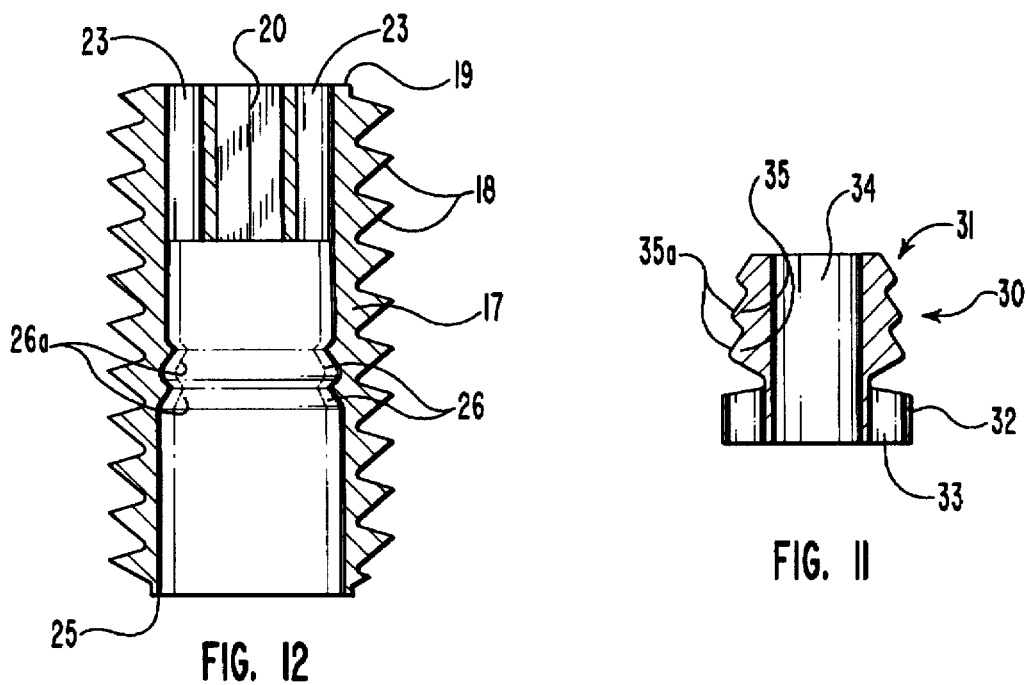
FIG. 12
FIG. 11
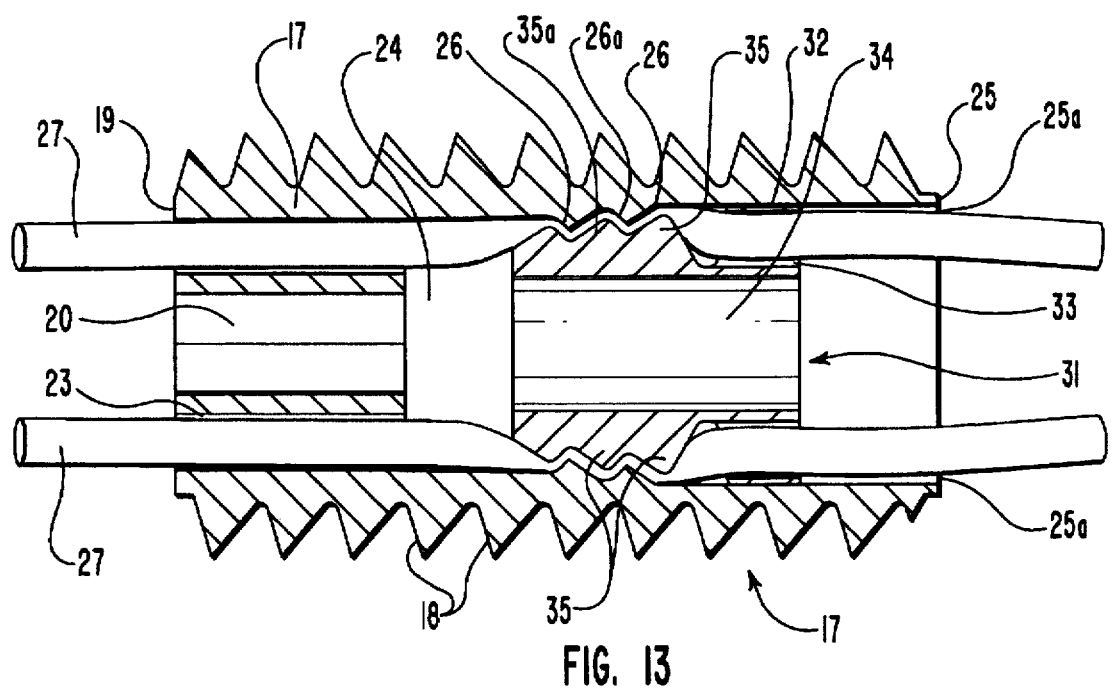
FIG. 13

LIGAMENT BONE ANCHOR AND METHOD FOR ITS USE

BACKGROUND OF THE INVENTION

1. Field of the Invention

This invention relates to anchor systems and particularly to endosteal devices for use in arthroscopic and open soft tissue surgical procedures performed on a patient to repair or replace a ligament or other soft tissue.

2. Prior Art

In a practice of an arthroscopic surgical procedure for repair and replacement of an anterior or posterior cruciate ligament, that the device of the invention is suitable for use in, it is a usual practice to form either straight tunnel, or non-straight sections or diverging tunnels that pass through the distal femur and proximal tibia and through the ligament connection sites or points of origin in the knee with both tunnel ends extending through the bone cortexes. For replacing a cruciate ligament, utilizing a tunnel procedure, with the knee bent, the tunnel sections are to be formed from the tibial tuberosity through the tibial and femoral points of ligament origin and into the femur to exit the femoral cortex adjacent the medial condyle. With the patient's skin opened to expose both tunnel ends and the adjacent bone cortex surfaces, a ligament is drawn through the tunnel, and the ligament ends secured within the tunnel sections, as with an interference screw or the like, or the ligament ends can be secured onto the adjacent cortex surfaces. In such a cruciate ligament repair or replacement procedure it is necessary to apply and maintain a tensile force on the ligament as one or both ends thereof are secured to the bones. In practice, where an interference screw is installed through a tunnel end, even with the ligament end maintained in tension, the screw installation tends to act against the applied tension, compromising the mounting. The present invention provides a mounting arrangement that is seated in the respective femoral and tibial tunnel sections prior to a tensile stress being applied to a replacement ligament fitted therein, insuring that the tensile stress on the ligament will remain as originally set.

One of the inventors has developed a number of cruciate ligament mounting arrangements, for example U.S. Pat. Nos. 4,772,286; 4,870,957; 4,927,421; 4,997,433; 5,129,902; 5,147,362; and Re. 34,293. None of which inventions, however, has provided for setting tension or adjusting the graft length on a cruciate ligament after the ligament mountings have been seated in the respective straight, non-straight or diverging tunnel sections, as the present invention provides for. Similarly, U.S. Pat. Nos. 4,605,414, 4,950,270 and 5,139,520, provide mounting devices and arrangements for setting ligament tension prior to seating mounting devices in bone tunnel sections in cruciate ligament replacement procedures.

Of course, a number of devices and procedures have heretofore been employed to secured ligament ends onto a bone surface after application of a tensile force thereto. Several of which are shown in U.S. Pat. Nos. 4,400,833; 4,467,478; 4,590,928; 4,597,766; 4,668,233; 4,773,417; and 4,834,752. None of which patents, however, has involved a mount for seating in a tunnel section with a ligament end secured thereto that is like the invention.

While several mounting arrangements have been developed for mounting in ligament tunnel ends, such have provided for turning end connectors of a prosthetic ligament therein, as shown in U.S. Pat. Nos. 4,301,551 and 4,744,793, and have not, as does the arrangement of the invention, provided for setting and maintaining a measured tension on an endosteal mounted ligament.

SUMMARY OF THE INVENTION

It is a principal object of the present invention to provide a bone anchor and system for its use for endosteal mounting and setting tension and length on a ligament, or the like, in a bone mass wherethrough straight, non-straight or diverging tunnels are formed.

Another object of the present invention is to provide a bone anchor for mounting and maintaining tension and length on a ligament, or the like, that is arranged for mounting in a tunnel section and includes individual sutures or shafts or a craddle of sutures or shafts pulled therethrough that connect on one end, to an end of a ligament, or the like, with the sutures or shafts to travel freely from bone anchor distal to proximal ends and provides a movable member to lock against those sutures or shafts within the anchor, prohibiting their return travel back through the anchor from proximal to distal ends so as to maintain a tension and length applied through the sutures or shafts.

Another object of the present invention is to provide a bone anchor for endosteally mounting a replacement ligament, or the like, such as a bone tendon bone ligament graft, that has at least one end secured to an end or ends of one or a number of sutures, or suture like strands, that are fitted to be drawn through the bone anchor that has been mounted into a ligament tunnel section, and for setting a tension and length through the suture or sutures on the ligament whose other end is secured within or at the cortex end of the other of the pair of ligament tunnel sections, the anchor of the invention including an internal movable member to lock to which sutures, prohibiting their withdrawal, and maintaining an applied tension and length.

Still another object of the present invention is to provide a bone anchoring device for both endosteally mounting a ligament end, or the like, within a ligament tunnel section and for locking a tension or length set into which ligament by prohibiting withdrawal of a single or plurality of sutures that attach may be formed into a craddle to the ligament end and pass through the invention.

Still another object of the present invention is to provide a bone anchoring device for mounting one end of a replacement ligament in one ligament tunnel section of a pair of ligament tunnel sections, and, with the other ligament end secured in the other ligament tunnel section, or adjacent bone cortex surface, provides for setting and maintaining a tension and length on the ligament.

Still another object of the present invention is to provide a bone anchoring device that is simple to install in a ligament graft type replacement procedure to both install a graft end in a tunnel section and for setting and maintaining a selected tension and/or length on the graft.

The present invention is in a device for endosteally mounting an end of a ligament graft, or the like, that may be a cruciate ligament, in a prepared ligament tunnel section and for setting and maintaining a tension or length on that ligament. Embodiments of bone anchoring devices are presented herein, that each have a cylindrical body with distal and proximal ends and is preferably threaded along its entire length for turning into a bone tunnel. The invention, however, may involve and incorporate, within the scope of this disclosure, other arrangements for securing the device in a bone tunnel. Each bone anchor includes a center longitudinal cavity formed therethrough, with a distal end that is sided to receive a turning tool.

Embodiment of a bone anchoring device of the invention each have a cylindrical body that is preferably threaded along its outer surface, but may be otherwise configured for mounting in and/or adjacent to a bone cortex surface of a ligament tunnel section. A longitudinal inner cavity is formed from the body distal end that is sided proximate to which end to receive a sided turning tool fitted therein for turning the bone anchor into a tunnel section. In a first embodiment the cylindrical body was a center cavity that expands from the sided portion into a concave section, or the like, therein. From the concave section, that is essentially a hemisphere, the cavity walls slope outwardly to the device proximal end forming, essentially, a flattened ellipse shape, or the like, that exits the anchor proximal end. A spherical ball, that may be scored across its surface, is contained within the cavity to roll towards and away from the concave section. Thereby, with a suture or plurality of sutures to form a craddle fitted through the device and across the spherical ball, the suture or sutures can be pulled freely through the device from distal to proximal ends. But, with a tension applied to the suture through the device distal end, the spherical ball will be pulled by that suture or sutures towards the cavity concave section, that is preferably serrated, pressing the suture or sutures against the cavity wall serrations and/or concave section, thereby prohibiting travel of the suture back through the device from proximal to distal ends. A tension applied to the suture through the bone anchor device of the invention will thereby permanently lock the suture within the device. Additionally, the spherical ball may include a spring force acting on it to force its gripping action.

A second embodiment of the invention incorporates, in the cylindrical body, several encircling spaced ridges and depressions formed in a midsection of the body center cavity that receive a plug fitted therein from its proximal end. The plug body of the second embodiment includes a plurality of encircling spaced ridges formed therealong, that are to oppose the cylindrical body spaced ridges, and includes a flat plug head end that extends across the device wherein a plurality of equal spaced radial holes are formed. Each plug head end hole is to receive a suture that has been passed through straight holes formed through the cylindrical body, adjacent and parallel to the longitudinal cavity, that exit a transverse wall formed across a mid-section thereof, travel alongside the plug body, across the plug spaced ridges and the cavity depressions, and exit the plug head end holes. The lip of the center cavity formed into the body at the proximal end may be inturned to maintain the plug head end inset therein. Similar to the arrangement of the second embodiment a sixth embodiment also includes a body center cavity. The body center cavity of the sixth embodiment, however, has smooth walls and is arranged to receive a plug fitted therein that consists of mirror image plug halves. The plug halves to receive a suture fitted therebetween, with the plug halves opposing surfaces urged against the suture, squeezing it therebetween, as the plug halves travel into the body center cavity.

Third, fourth and fifth embodiments of the bone anchoring device are like the first embodiment, except, rather than a spherical ball, a transverse rod or cylinder is axially mounted as the third embodiment in opposing tracks across the center cavity to turn and to travel back and forth along the tracks. The transverse rod or cylinder is arranged to move into engagement with the suture or sutures fitted through the center cavity and over the rod or cylinder, clamping the suture or sutures against the cavity walls that are preferably serrated. Additionally, as a fourth embodiment, a cam is pivotally mounted to pivot across the center cavity, such that a serrated end surface thereof clamping against a suture or sutures in a fourth embodiment. Also, as a fifth embodiment, a pulley of a turn back device which may be fixed or rotating may cross the cavity to receive a suture passed through a first body passage and therearound that exits past a ball aligned across a second body passage that the suture is fitted through. In this fifth embodiment the suture travels back upon itself.

In practice, a single, or a number of sutures that form a craddle of sutures are for connection to a ligament end, such as a bone end of a bone tendon bone ligament graft, with the suture ends then threaded through the cylinder holes or hole, of the bone anchor, to travel alongside and over the spherical ball, or alongside the plug body and across and between the ridges or over a section of the cylindrical rod or roller, or between plug halves, or beneath the end of a cam and out of the plug head end holes and/or out of the cylindrical body proximal end, or, as in the fifth embodiment into the cylinder and back upon itself.

In all the preferred embodiments of the bone anchor of the invention, a tool receiving cavity is preferably formed into the body distal and proximal ends to receive a turning tool, such as an allen wrench fitted therein, for turning the device into the ligament tunnel section. To perform which turning, the cylinder with or without the sutures fitted thereto is seated onto the turning tool end. Thereat, the anchor is twisted relative to the suture or sutures for turning into the ligament tunnel section making approximately the same number of turns as the number of turns that the suture is twisted to straighten the suture or sutures. Which pretwisting, of course, is less important where a single suture is employed. The suture or sutures extend from the device proximal end, or as in the fifth embodiment, exit the same end as they or it enters, and are passed out of a cortex tunnel end to be pulled by a surgeon/operator. By pulling which suture or sutures, the ligament end whereto the suture or sutures are connected is pulled into the femoral and/or tibial tunnel section wherein the device is seated, pulling a ligament, or the like, therein. The sutures may be pulled to apply a desired tensile stress. In pulling the sutures through the device, the spherical ball, plug, transverse rod or pivoting cam plug halves or the turn back device of the first, second, third, fourth, fifth and sixth embodiments is moved in the device longitudinal cavity towards its proximal end, with the suture or sutures traveling freely therethrough. Whereafter, with a tension set through the suture or sutures, the spherical ball, plug, transverse rod, pivoting cam, plug halves or lock ball of the turn back device will be pulled back into the longitudinal cavity. Thereby, in the first, third, fourth, fifth and sixth embodiments, the spherical ball, transverse rod, pivoting cam, plug halves or lock ball will have moved to crush the suture against the cavity wall, between the plug halves opposing faces, or the like, locking the suture or sutures in place. In the second embodiment, the respective plug body and cavity ridges will crush the suture or sutures therebetween, locking the suture or sutures in place. Thereafter, the suture or sutures that extend beyond the device proximal end can be cut and the ports formed into the knee in the surgical procedures closed.

Optionally, with respect to the second embodiment, to provide for releasing the sutures to relax tension on the ligament, allowing the cut suture ends to be pulled back through the device, the plug is threaded through an axial opening to receive a set screw turned therethrough. A tool is provided for fitting into the set screw for turning it inner trans plug to engage the cylinder inner transverse wall urging the plug towards the cylinder proximal end so as to release the binding engagement exerted on the suture or sutures by the respective plug body and cavity ridges. With, in the first, third, fourth, fifth and sixth embodiments, to release the suture or sutures, a rod end can be fitted through the device distal end to engage the spherical ball, cylindrical rod, pivoting cam, plug halves, or lock ball to urge it away from the suture or sutures surfaces.

DESCRIPTION OF THE DRAWINGS

In the drawings that illustrate that which is presently regarded as the best modes for carrying out the invention:

FIG. 11 is a longitudinal sectional view of the plug head end taken within the line 11—11 of FIG. 10;

FIG. 12 is a longitudinal sectional view of the cylindrical body taken within the line 12—12 of FIG. 10;

FIG. 13 is a longitudinal sectional view of the cylindrical body with the plug head end seated therein showing opposing ridges of the cylinder and plug head body engaging and locking sutures fitted therethrough, illustrating the invention mounting the sutures configured to provide a locking engagement with the sutures fitted therethrough;

DETAILED DESCRIPTION OF THE INVENTION

Figure 6:
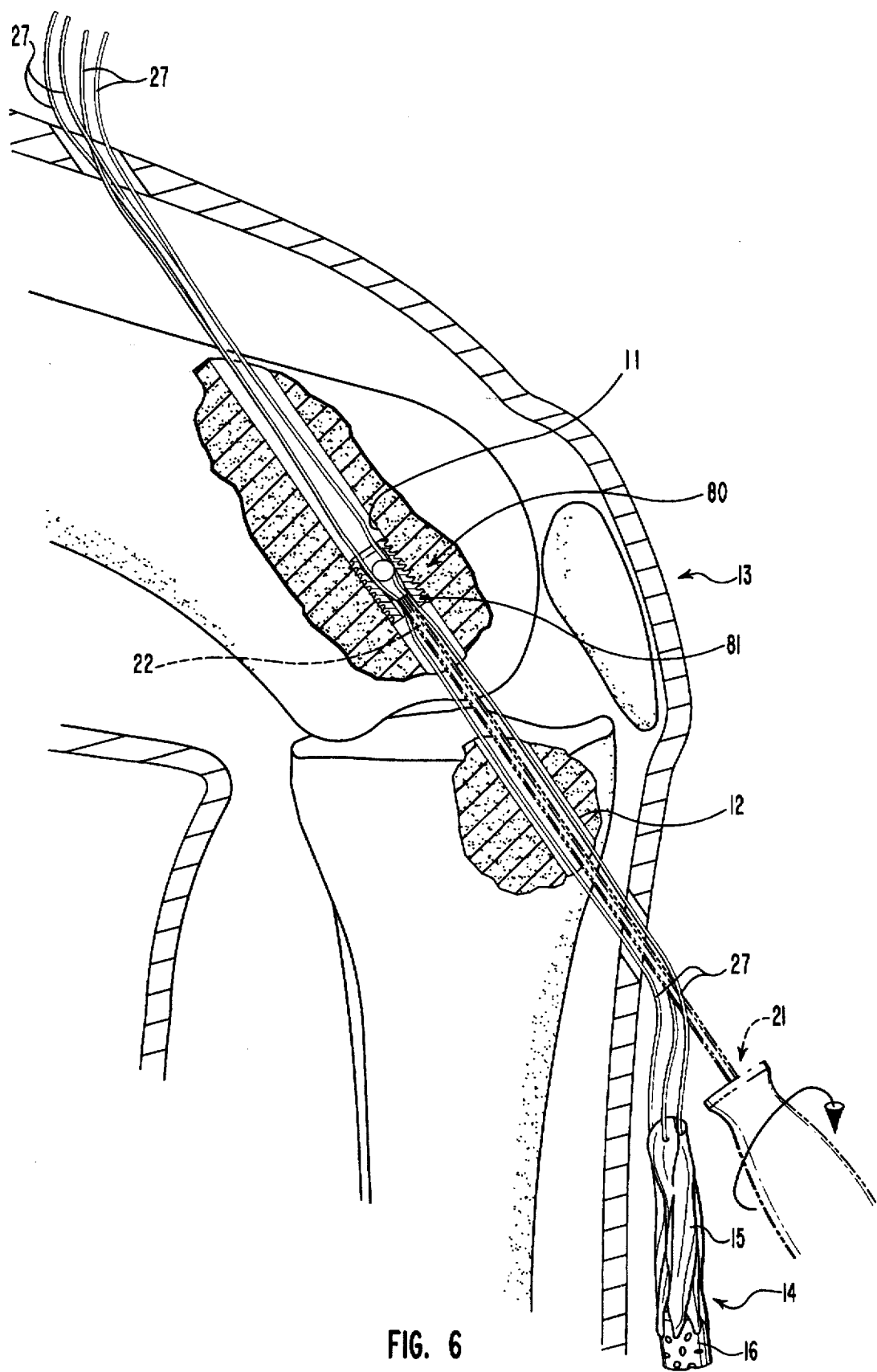
FIG. 6, shows the first embodiment of FIG. 1 of the invention being turned by a tool fitted into its distal end into a femoral ligament tunnel section with the sutures threaded therethrough and extending from the tunnel femoral cortex end with the opposite suture ends shown secured to an end of a ligament graft.

A first embodiment of a bone anchor 80 of the invention, hereinafter referred to as anchor, is shown in FIG. 6, being installed in an arthroscopic surgical procedure for repair or replacement of an anterior cruciate ligament. In the procedure, a ligament replacement tunnel, that is shown herein as a straight tunnel but may be non-straight, diverging, or the like, within the scope of this disclosure, is formed as femoral and tibial tunnel sections 11 and 12, respectively, in a patient's knee 13, that form the straight tunnel when the knee is bent approximately ninety (90) degrees. In the procedure, the patient receives a replacement ligament graft 14, as a ligament 15 having a bone end 16, that is to be secured, under tension, in or through the tunnel sections 11 and 12, with the graft to cross the knee 13 through the points of ligament origin.

The anchor 80, as shown in FIGS. 1 through 5, is turned by a tool 21, shown in FIG. 6, into femoral tunnel section 11 in a procedure for replacing a patient's anterior cruciate ligament. It should however be understood that the anchor 80 could be mounted in the tibial tunnel section 12, or could be used in a procedure for replacing a patient's posterior cruciate ligament, or in another surgical procedure for securing a suture, or the like, under tension in a tunnel formed in a bone mass within the scope of this disclosure. A description of the arrangement and use of anchor 80 should, therefore, be taken as a description for such other use or uses also.

Figure 1:
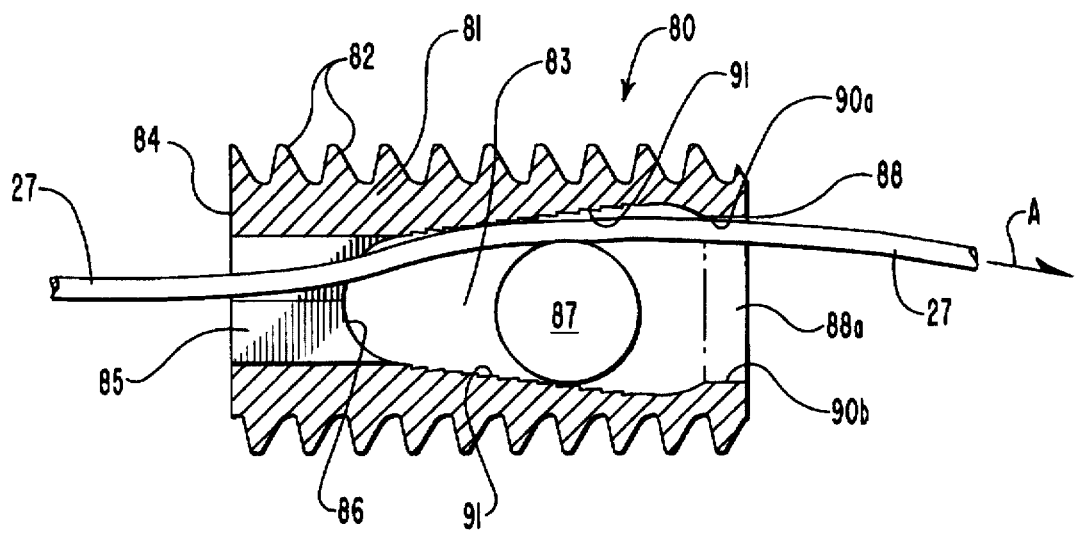
FIG. 1 is side elevation longitudinal sectional view of a first embodiment of a bone anchor of the invention, showing a center longitudinal cavity wherein a spherical ball is contained and with a suture fitted therethrough.
Figure 2:
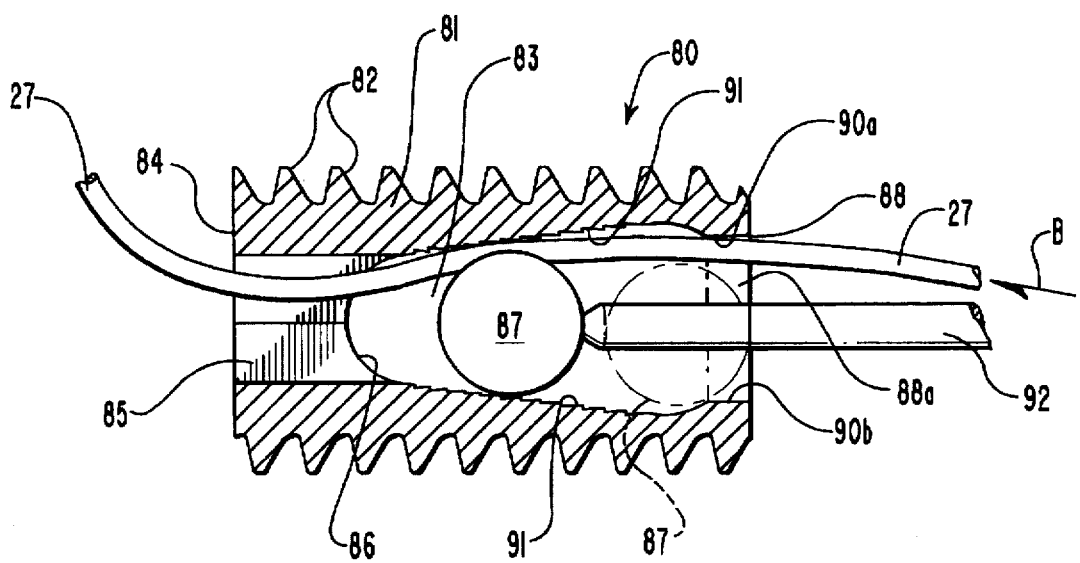
FIG. 2 is a view like that of FIG. 1 only showing the spherical ball as having moved towards a concave end of the cavity against the suture, locking the suture in place.
Figure 5:
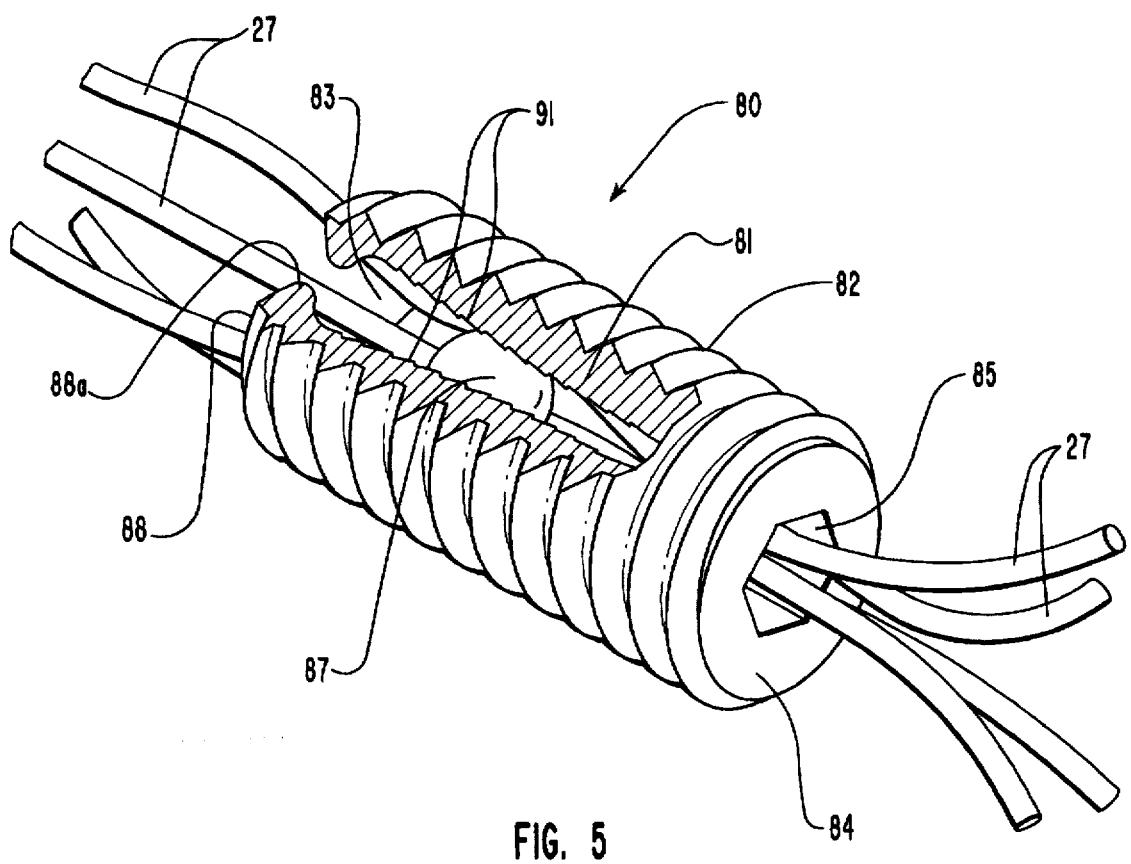
FIG. 5 is a profile perspective view of the bone anchor of FIG. 1 showing a longitudinal sectional view removed from the cylindrical body exposing the ball therein with a plurality of sutures shown fitted therethrough.
Figure 24:
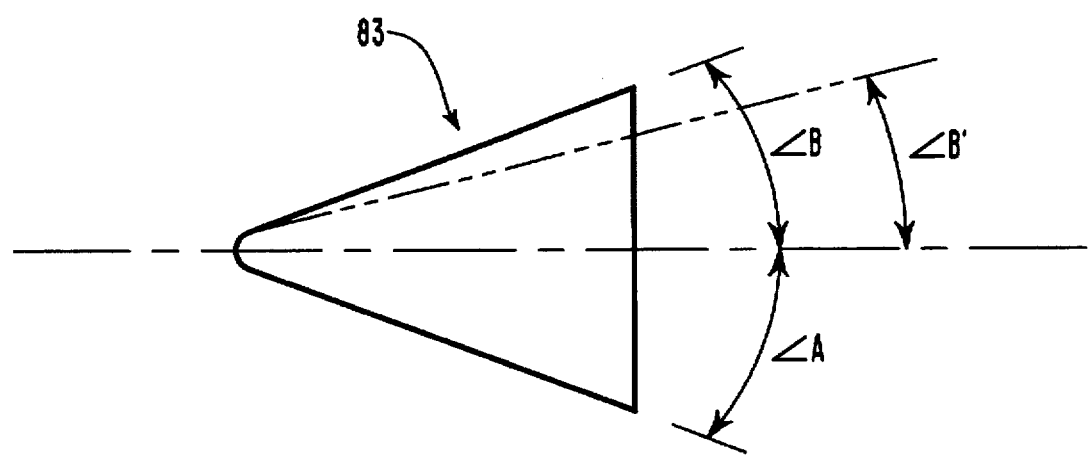
FIG. 24 is a schematic of showing different possible angle relationships of the spherical ball of FIGS. 1 through 9 within the body center longitudinal cavity.

The first embodiment of a bone anchor 80 of the invention is shown in FIGS. 1 through 5, and being installed in FIGS. 6 through 8, hereinafter referred to as anchor 80. Anchor 80 is preferably a cylinder body 80 that is threaded at 82 along its outer surface for turning into a tunnel section, as shown in FIG. 6. Though, within the scope of this disclosure a mounting arrangement other than threads 82 for securing the anchor in a tunnel section, such as an expanding collar, outwardly projecting spikes, or the like, can be utilized for seating the anchor 80. Also, it should be understood the other anchor embodiments 10, 40, 100, 120, 135 and 150, as set out hereinbelow, could likewise be arranged for other than screw mounting within the scope of this disclosure. A center longitudinal cavity 83 is shown formed through the anchor 80 that exits a distal end 84, as shown in FIGS. 1, 2 and 5. Which cavity 83 is shown as centered but may be off-center within the scope of this disclosure. Sides 85 are formed in the distal end that are for receiving a turning tool like the sided turning tool 21 shown in FIG. 6, that is fitted therein to turn the threads 82, that are formed along the anchor 80 body 81, into the knee 13 femoral tunnel section 11. The longitudinal cavity 83, within the body 81, is counter bored or otherwise shaped to form a conical end section 86, as shown in FIGS. 1 and 2, that functions as a seat for a spherical ball 87, as shown in FIGS. 2 and 5. Which cavity 83 is illustrated also in FIG. 24 that shows an angular relationship that the cavity can be off-set from the longitudinal center of body 81. Wherein, with angle B equal to angle A the cavity 83 is centered, and where angle B' is less than angle A the cavity is not centered.

Figure 3:
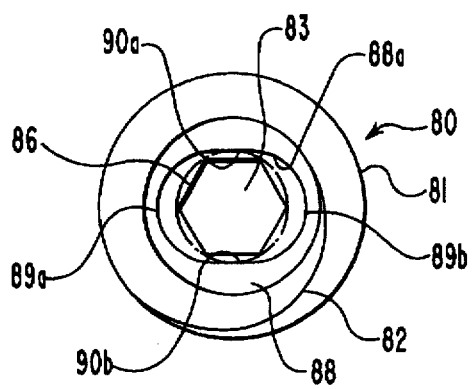
FIG. 3 is a top end view of the bone anchor of FIG. 1.
Figure 4:
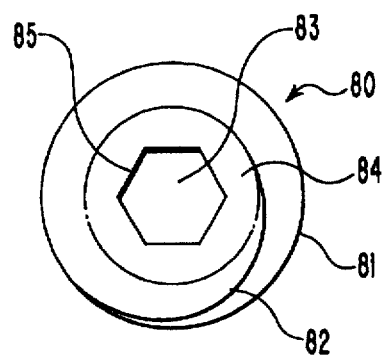
FIG. 4 is a bottom end view of the bone anchor of FIG. 1.

From the conical section 86 the cavity sides slope outwardly into opposing sides 89a and 89b, and top and bottom sides 90a and 90b, that preferably include serrations 91 formed at spaced intervals therealong that end at an anchor body top or proximal end 88. The shape of which cavity 83 as it exits the proximal end 88 preferably is a flattened ellipse, as shown in FIG. 3. Which proximal end is shown as having been turned down or crimped at edge 88a around which cavity 83 end such that the distance between the top and bottom sides 90a and 90b will be less than the diameter of the spherical ball 87. Alternatively, the cavity proximal end 88, around edge 88a, can be grooved to receive a wire spring, or the like, seated therein for retaining the spherical ball 87. So arranged, the spherical ball 87 is contained within the cavity 83 to roll between the conical section 86 and the cylinder proximal end 88 edge 88a.

Shown in FIGS. 1 and 2, a suture 27, that may be round, flat, or other shape within the scope of this disclosure, is fitted through the anchor 80, with a plurality of sutures 27 shown fitted through the anchor 80 of FIG. 5, from the anchor distal end 83 sided opening 85, passing over the spherical ball 87 and exiting the anchor proximal end 88. In practice, with the suture or sutures 27 pulled through the anchor 80, as illustrated by arrow A, in FIG. 1, the spherical ball 87 will be rolled away from the conical section 86, as shown. However, when a tensile force is applied to the suture or sutures 27, as illustrated by arrow B in FIG. 2, the suture will roll the spherical ball 87 towards the conical section 86 engaging a section of the suture, that is trapped between the ball surface and the serrations 91 that are formed along the center cavity wall, locking the suture in place. As required, an end of a rod 92 can be fitted through from the anchor top end 88 into the cavity 83 to engage the spherical ball 87 and push it towards the conical section 86, tamping the spherical ball 87 into suture 27, insuring that it engages the suture, forcing it against the serrations 91, as shown by arrow B. Also, the spherical ball 87 surface can be scored to further increase a friction force with the sutures 27.

Figure 9:
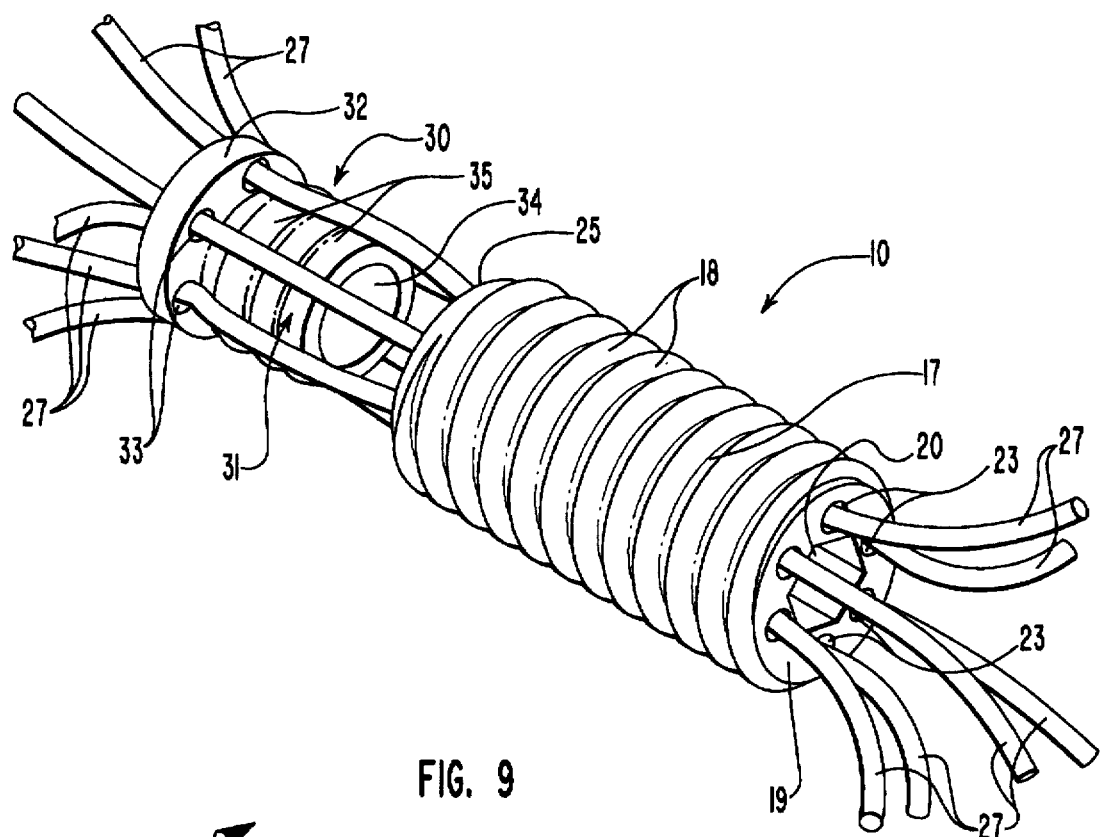
FIG. 9 is an exploded profile perspective view of a second embodiment of a bone anchor of the invention shown with a craddle of sutures threaded therethrough.
Figure 10:
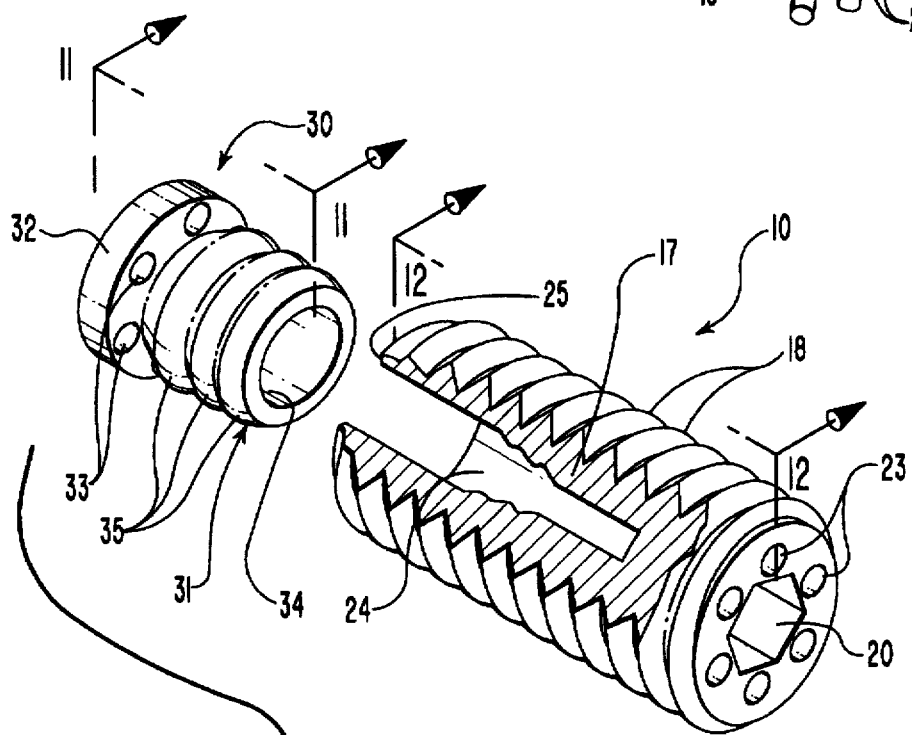
FIG. 10 is an exploded view like that of FIG. 9 showing a longitudinal section removed from a cylindrical body and with the sutures removed.

FIGS. 9 and 10 show a second embodiment of a bone anchor 10, hereinafter referred to as anchor 10, that includes a cylindrical body 17 that is threaded along its entire length at threads 18 and is open through a longitudinally cavity 24. The cavity 24, adjacent to a cylinder bottom or distal end 19, is formed to have sides as a tool receiving section 20 of cavity 24, which tool receiving section 20 is shown as having six sides to accommodate an allen wrench type of tool shown as being a hexagonal sided tool end 22 that is formed in an end of driver 21, shown in FIG. 6. A number of identical spaced radial holes 23 are formed longitudinally through anchor distal end 19, around and parallel to the tool receiving section 20 of cavity 24 that, as shown best in FIG. 13, extends through an upper portion of the cylinder through an interior wall and into an open area of cavity 24 that extends to an anchor cylinder top or proximal end 25. Within the open area of cavity 24 a number of spaced ridges 26 are formed, that are each shown as having a triangular shape with long sides 26a thereof facing towards the cylinder proximal end 25. The function of which ridges long sides 26a is for providing surfaces to clamp against sutures 27 when opposing outer ridges 35 of a plug 30 are urged thereagainst, as set out below.

Like the turning of anchor 80, as shown in FIG. 6, tool 21 is preferably used to turn the anchor 10 into femoral tunnel section 11, with the threads 18 formed along body 17 turning into the tunnel section wall. Sutures 27 that connect onto one end to the ligament graft 15 are formed into a craddle to support ligament. Shown in FIGS. 9 and 13, for anchor 10, the sutures 27 are fitted through the anchor 10 and extend from the proximal end 25 to beyond the femoral tunnel cortex end. Accordingly, a surgeon/operator, by pulling on the suture 27 ends that extend from the femoral cortex end, can pull the ligament graft 14 through the tibial tunnel 12, as shown in FIG. 7 for anchor 80, and into the femoral tunnel section 11 to where the sutured ligament 15 end is proximate to the cylinder distal end 19, as shown in FIG. 8 for anchor 80. Whereat, a screw 28 can be turned through the side of the proximal tibia, into the tibial tunnel section 12, that travels into the bone end 16 of the ligament graft 14, above a bone bottom surface 16a. A set screw type mounting of the graft tibial end in the tibial tunnel section is thereby provided. Whereafter, a tension is applied through the sutures 27 to the ligament 15 sutured end, and that tension is maintained, as set out below.

Shown in FIGS. 9 through 13, the anchor 10 is fitted with a plug 30 that functions to allow the sutures 27 to be pulled therethrough, pulling the ligament graft 14 through the tibial tunnel and into the femoral tunnel to where a tension is applied to the graft. The plug 30, as shown in FIGS. 9, 10, 11 and 13, includes a cylindrical body 31 that is capped or crowned by a disk head 32 across its proximal end. The disk head 32 includes equal spaced radial holes 33 formed therearound that, as shown in FIG. 9, pass the individual sutures 27 therethrough. Plug body 31 includes a longitudinal hole 34 formed therethrough from distal to proximal ends, and has a plurality of triangular shaped ridges 35 formed at spaced intervals along and encircling the body 31. The plug 30 is for fitting through the longitudinal opening in the cylindrical body 17 proximal end 25 and seating in the longitudinal cavity 24, forward of the interior wall. The plug 30 is to slide in the cavity 24 such that long sides 35a of ridges 35 oppose long sides 26a of the cylindrical body ridges 26. The respective ridges long sides 26a and 35a oppose one another and are urged together when the plug 30 is pulled into the cylindrical body 17 cavity 24, crushing the sutures 27 therebetween, as shown best in FIG. 13. Travel of the plug 30 in the cylindrical body cavity 24, moves the respective ridges long sides 26a and 35a into engagement with the sutures 27 fitted therebetween, is provided by applying tension to the ligament graft 14 through the sutures 27, as illustrated for anchor 80 in FIG. 8, and as set out below. Additionally, the plug 30 may be pushed, as with the end of tool 21, into engagement with sutures 27 as a tension is applied to the ligament graft, to initiate suture engagement.

Figure 8:
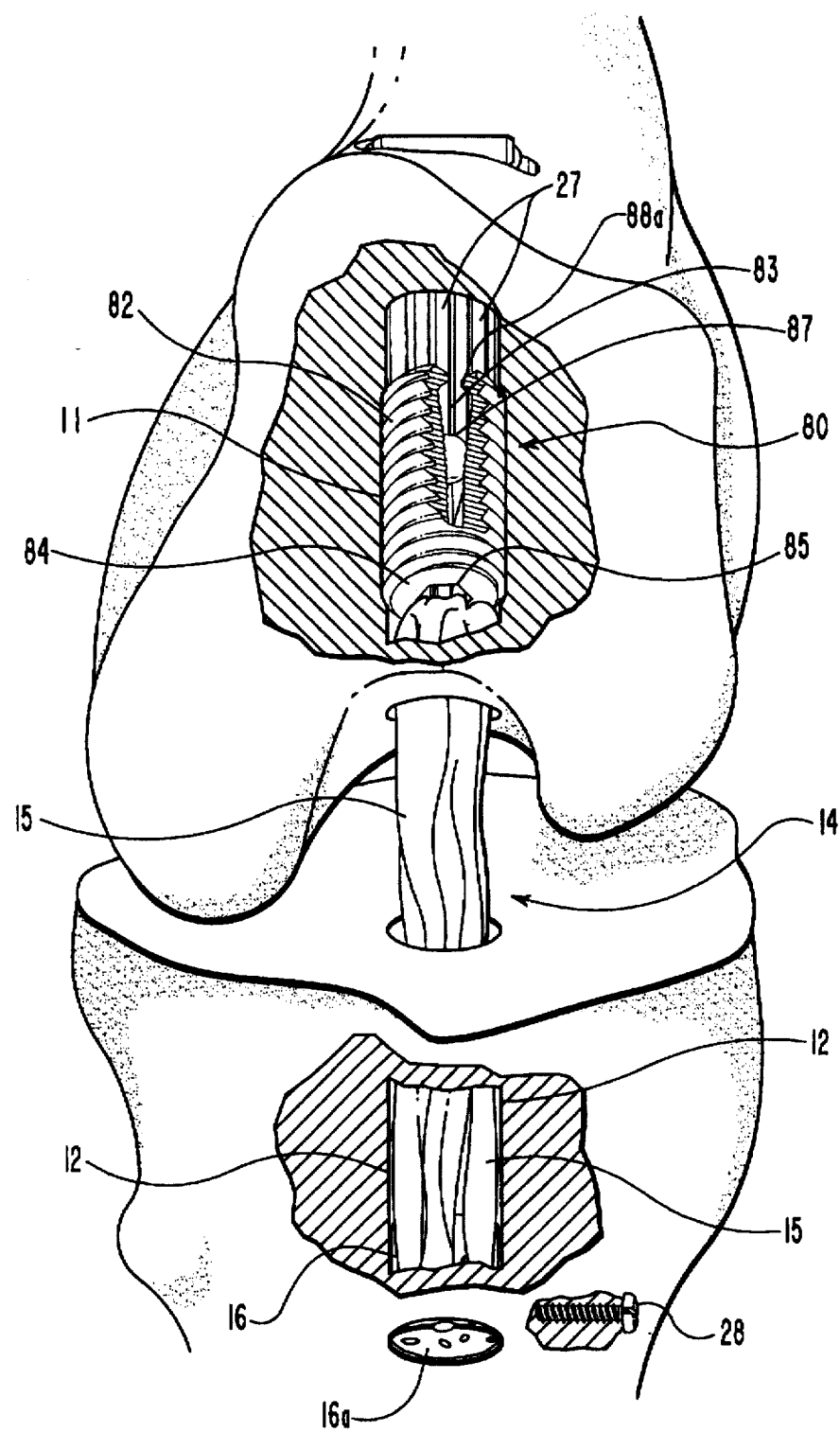
FIG. 8 is a view like that of FIG. 7 with the ligament shown as having been fully drawn into the femoral tunnel section to engage the inner end of the cylindrical body and showing a screw being turned into a bone end of the ligament graft for mounting the graft tibial end in the tibial tunnel section.

With the ligament graft tibial end secured in the tibial tunnel section 12, as shown for anchor 80 in FIG. 8, or in the femoral tunnel section, with anchor 10 so installed, the surgeon/operator pulls on the sutures 27 ends that extend out from the femoral tunnel section 11 or tibial tunnel section 12 cortex end to place the ligament graft 14 in tension. In that tensioning, the sutures 27 are pulled across and move apart the respective opposing rides long sides 26a and 35a, with the plug 30 traveling within the cylindrical cavity 24 to the proximal end where further travel is blocked by an edge 25a of the proximal end 25 that is turned or bent into the cavity. Additionally, other arrangements, such as utilization of a lock ring fitted into a cavity groove, whereagainst the plug head end 31 edge will engage, not shown, or the like, could be used to maintain the plug 30 in cavity 24 within the scope of this disclosure.

When the desired ligament tension is obtained, upon release of the pulling force on the sutures 27, plug 30 is urged into the cavity 24 such that the respective ridges long sides 26a and 35a move towards one another crushing the sutures 27 therebetween. The sutures 27 are thereby locked between the ridges long sides 26a and 35a prohibiting suture travel, permanently locking the ligament graft 14 in place, under tension in the femoral or tibial tunnel sections 11 or 12. Thereafter, the sutures can be cut above the anchor 10 proximal end 25 and the knee ports through the patient's skin closed with the ligament graft under tension to receive tibial and femoral bone matter growing thereto.

To release the anchor 10 the ligament graft 14 from the anchor 10 tension on the sutures 27 must first be removed. Such can involve release of the graft tibial end, cutting of the graft in the knee joint, or the like, whereafter the cylindrical body can receive the turning tool 21, as shown in FIG. 6 for anchor 80. Which tool 21 can then be used to either turn the anchor through the femoral or tibial tunnel, exiting the cortex, or it can be turned back into the knee joint to be captured and removed therefrom. As an alternative to that procedure, the invention provides a ligament bone anchor 40, that is a variation of anchor 10, hereinafter referred to as anchor 40, and is shown in FIGS. 14 through 17.

Anchor 40 is like anchor 10 in that it also includes a cylindrical body 41 that is configured like the anchor 10 and has threads 42 formed along the outer surface, and includes a longitudinal cavity 43. A lower end of which longitudinal cavity 43 is sided at 44, exiting a bottom or distal face 45 that is for receiving turning tool 21. Which longitudinal cavity 44 includes spaced ridges 46 that are like ridges 26. Parallel spaced radial holes 47 are formed through the bottom face 45 that exit through an interior wall 48, as shown best in FIGS. 16 and 17. As shown, a plug 50, like plug 30 is provided for fitting through the body proximal end and includes a cylindrical body 53 with a disk head end 54 wherethrough spaced radial holes 55 are formed. The plug 50 includes spaced ridges 56 formed around the body 53 outer surfaces that are like and function the same as plug 30 ridges 35. Plug 50, distinct from plug 30, however, is threaded at 52 through a center longitudinal cavity 51.

Figure 14:
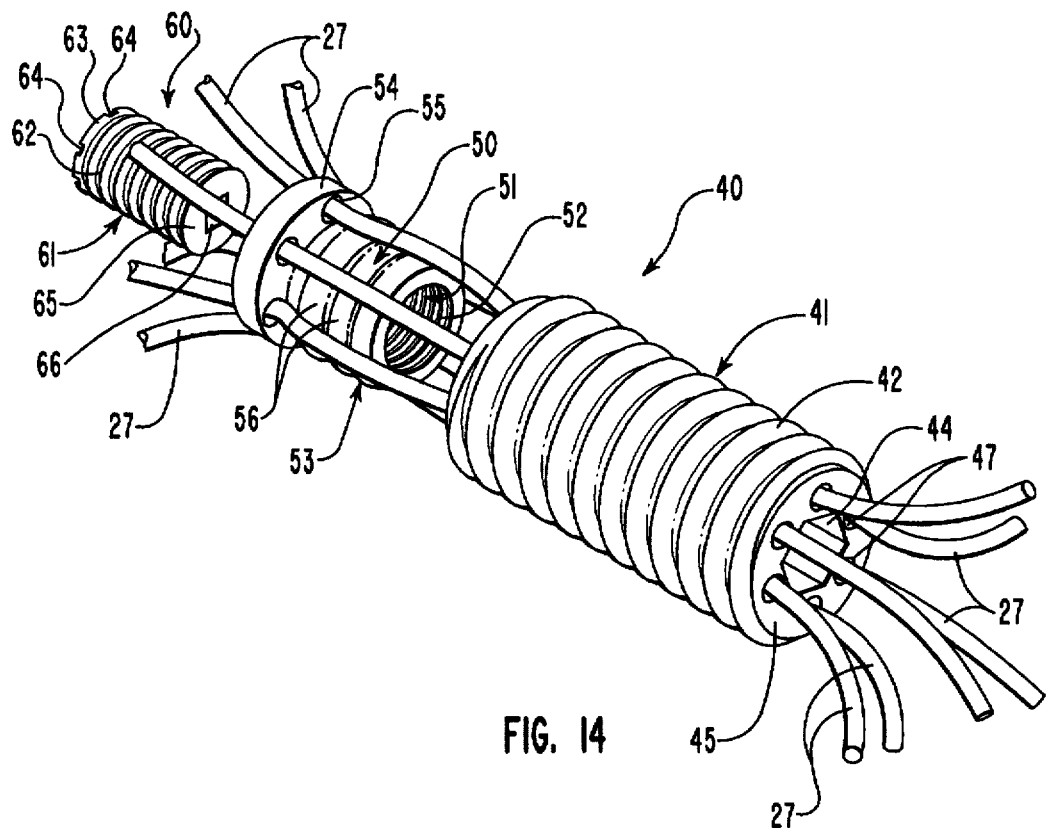
FIG. 14 is a view like FIG. 9 showing the ligament bone anchor plug as having had a longitudinal threaded hole formed therethrough to receive a set screw aligned for turning into plug threaded hole proximal end.
Figure 15:
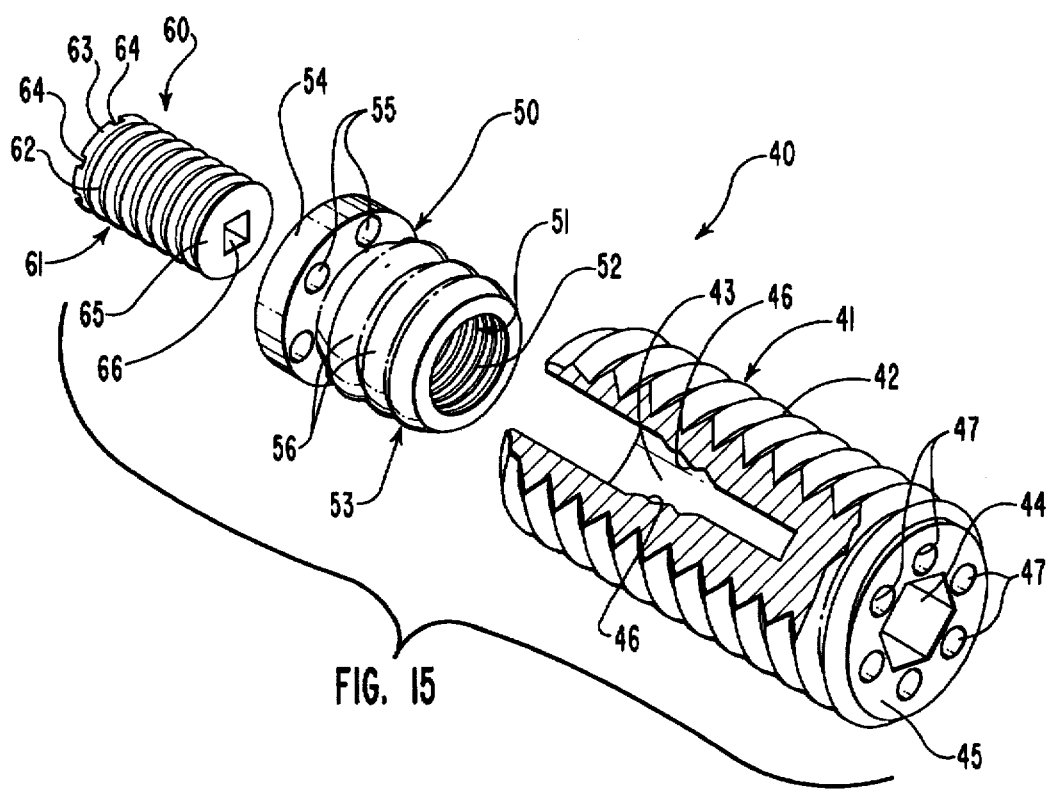
FIG. 15 is a view like that of FIG. 9 showing the ligament bone anchor of FIG. 10 with the set screw aligned for turning into the plug threaded hole proximal end.
Figure 16:
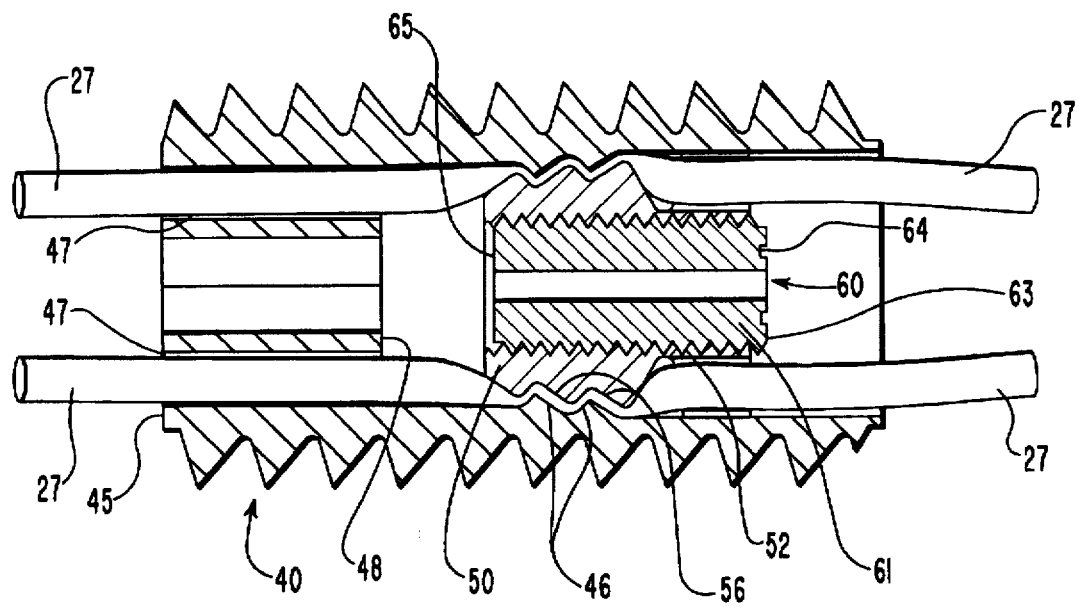
FIG. 16 is a view like that of FIG. 13 showing the set screw of FIGS. 14 and 15 being turned into the plug threaded hole from the proximal end.

The plug 50 threads 52 are for receiving a set screw 60 turned therein. The set screw 60 is shown in FIGS. 14 and 15 aligned for turning into the plug and, in FIG. 16 is shown turned therein. FIG. 16, like FIG. 13, shows the plug 50 seated in the cylindrical body 41 so as to compress sutures 27 fitted therethrough between the respective ridges 46 and 56 to lock the sutures 27 in the anchor 40. Functioning of plug 50, it should be understood, is like that as described hereinabove for plug 30 as described with respect to the operation of anchor 10.

Figure 17:
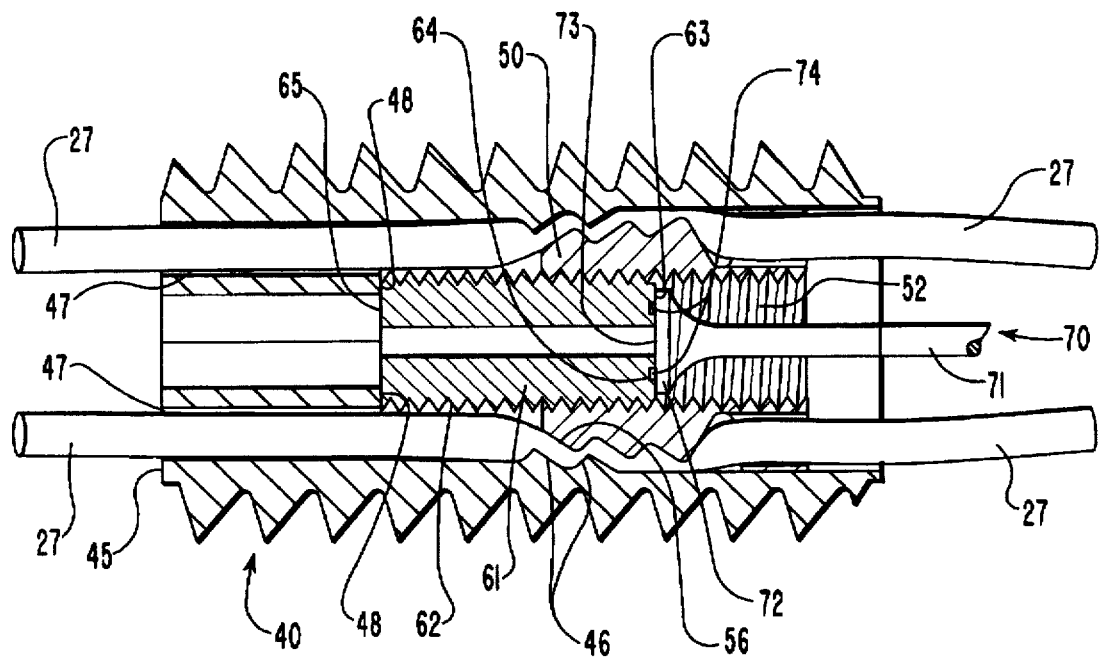
FIG. 17 shows the view of FIG. 11 with the set screw shown as having been turned by a tool through the plug and exiting its distal end so as to engage a forward face thereof with an inner wall of the cylindrical body, urging the plug away therefrom to move the respective plug body and cylinder ridges apart, releasing the sutures to allow them to be pulled out of the invention distal end releasing a tension on the ligament end.

FIG. 17 shows the set screw 60 as having been turned through the plug 50 by turning a tool 70 that has been fitted to an anchor top or proximal end 63 to where the set screw 60 bottom or distal end 65 has engaged the interior wall 48 formed in the anchor cylindrical body 40. After which engagement of the set screw distal end 65 with interior wall 48, with continued turning of the set screw 60 through plug 50, the plug 50 is moved away from interior wall 48. The respective opposing surfaces of the ridges 46 and 56 are thereby moved away from one another, releasing the sutures 27, that can then be pulled out of the anchor bottom end 45.

To provide for turning the set screw 60 into the plug 50, as shown in FIG. 17 and described above, the plug proximal end surface 63 includes a plurality of spaced slots, depressions, or holes 64 formed therein that are for receiving short posts 74 that extend at right angles outwardly from a flat face 73 of a disk head end 72 of the tool 70. The tool 70 preferably includes a straight shaft 71 that is secured, on one end, to the disk head end 72 and includes a handle, not shown, on its other end that is for turning by a surgeon/ operator. In operation, the surgeon/operator fits the disk head end 72 of tool 70 through the femoral or tibial cortex tunnel end and into the femoral or tibial tunnel, traveling between the sutures 27, toward the cylindrical body 41 proximal end with the set screw 60 turned into plug 50. The head end 72 contacts the set screw proximal end 63. The surgeon/ operator then turns the tool 70 to where the outstanding posts in the flat face 73 align with and fit into the holes 64 in the set screw proximal end face 63. Thereafter, with continued turning of the tool 70, the set screw 60 is turned into the plug 50 to the attitude shown in FIG. 17, releasing pressure exerted between the ridges 46 and 56 on the sutures 27, so as to allow which sutures to be pulled back through the anchor 40 and through the knee joint.

Figure 18:
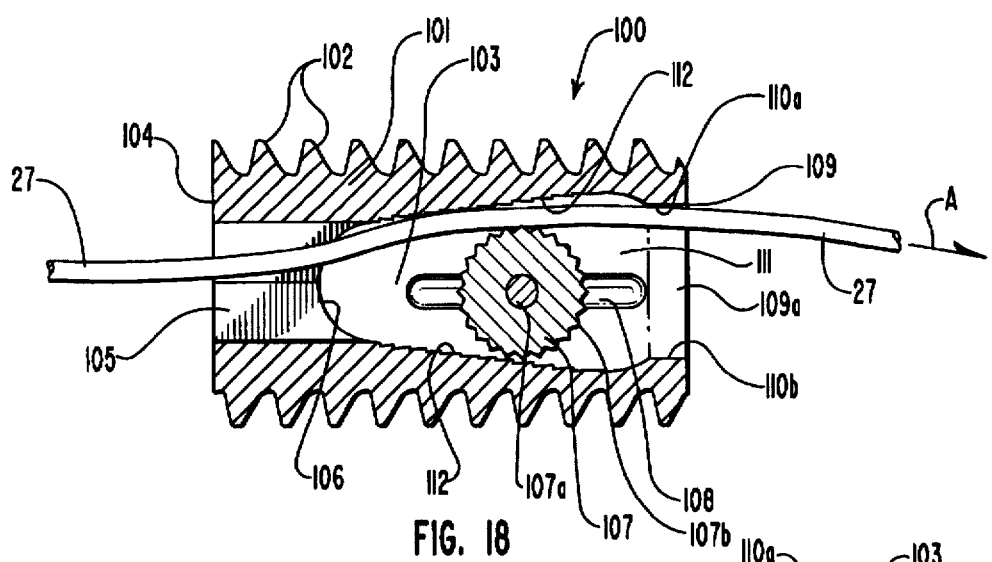
FIG. 18 is a side elevation longitudinal sectional view of a third embodiment of a bone anchor of the invention, showing a body with a center longitudinal cavity wherein a transverse rod or roller is positioned to be movable along tracks in which cavity and with a suture shown fitted therethrough.
Figure 20:
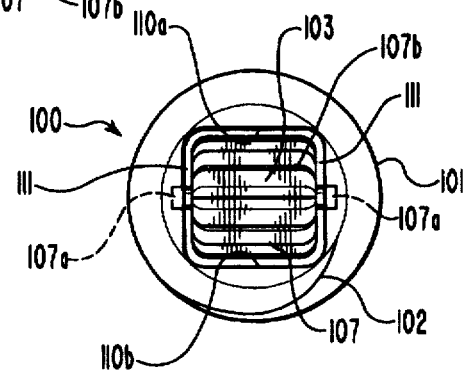
FIG. 20 is a top end view of the bone anchor of FIG. 18, showing, in broken lines, the center cavity cross section.
Figure 19:
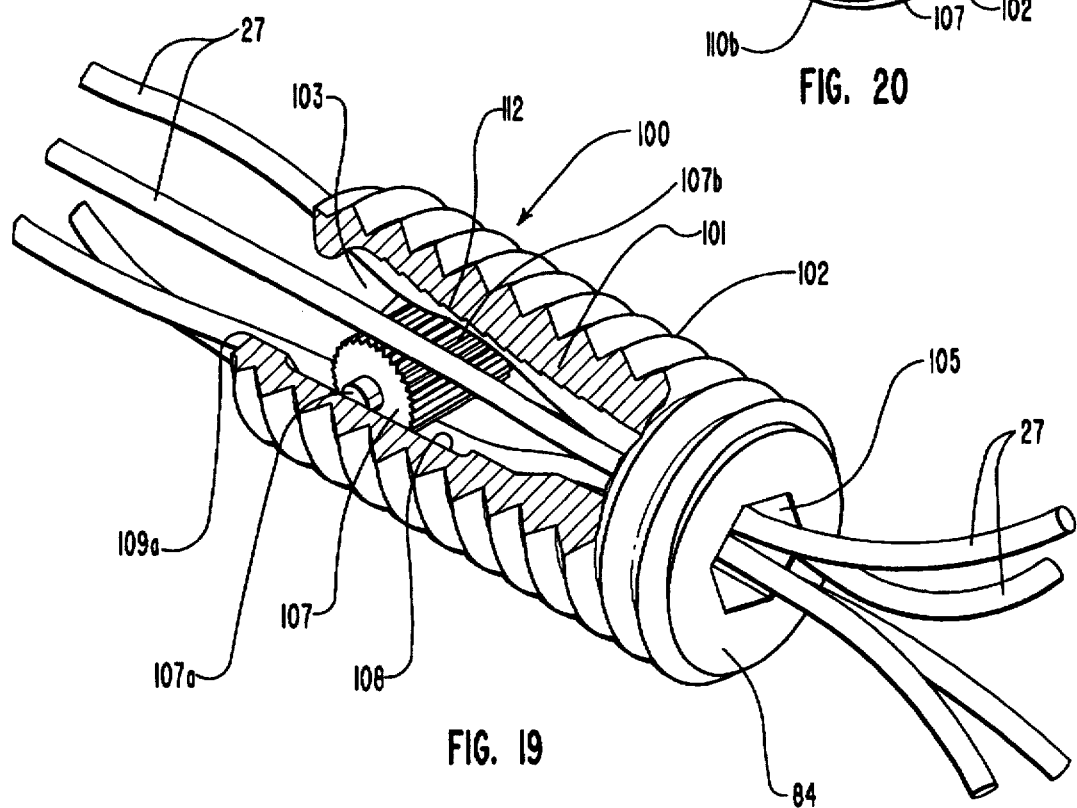
FIG. 19 is a side elevation perspective view of the transverse rod or roller removed from the center cavity of the anchor of FIG. 18.

A third embodiment of a bone anchor 100, hereinafter referred to as anchor 100, is shown in FIGS. 18 through 20. Anchor 100 is like anchor 80 in that it has a cylindrical body 101 that is preferably threaded at 102 for turning into a ligament tunnel section, as illustrated by anchor 80 in FIGS. 6, 7 and 8. A longitudinal cavity 103 is formed through anchor body 101 that exits an anchor distal end 104, wherein are formed sides 105 for receiving a turning tool, like the turning tool 27 of FIG. 6, fitted therein. The longitudinal cavity is rounded at a distal end forming a curved end section 106. Longitudinal cavity 103 walls extend therefrom to a proximal end 109 to have, unlike anchor 80, a square or like shape, as shown in FIG. 20, with top and bottom walls 110a and 110b and opposite sides 111. Which top walls 110a and 110b may include serrations 112 formed therealong. Shown in FIG. 18, the opposite walls 111 each have a longitudinal slot 108 formed therein to accommodate stub axles 107a that extend at right angles from opposite ends of a transverse rod or cylinder 107, identified herein as a cylinder. The cylinder 107 is to function like spherical ball 87 of anchor 80, rolling along stub axles 107a in slots 108, between the curved end section 106 and the cylinder proximal end 109 that is inturned at 110a to maintain the cylinder 107 therein. Cylinder 107 travel, like that of spherical ball 87, is responsive to suture 27 travel therethrough, illustrated as arrow A. The cylinder to roll towards the proximal end as the suture is pulled out of the anchor proximal end, illustrated as arrow A, and towards the curved end section 106, when a tension is exerted on the suture through the anchor distal end 104. The suture tension pulls the cylinder back towards the curved end section 106, crushing a section of the suture or sutures 27 that pass over the cylinder 107 outer surface against serrations 112, functioning like the spherical ball 87 as described for anchor 80. Further to aid in adherence of the cylindrical surface to the suture 27 the cylindrical surface is preferable scored thereacross, shown at 107b, shown as grooving, serrations, or the like, for increasing friction with the suture. Which scoring, as set out above, can also be included on the spherical ball 87, within the scope of this disclosure.

Figure 21:
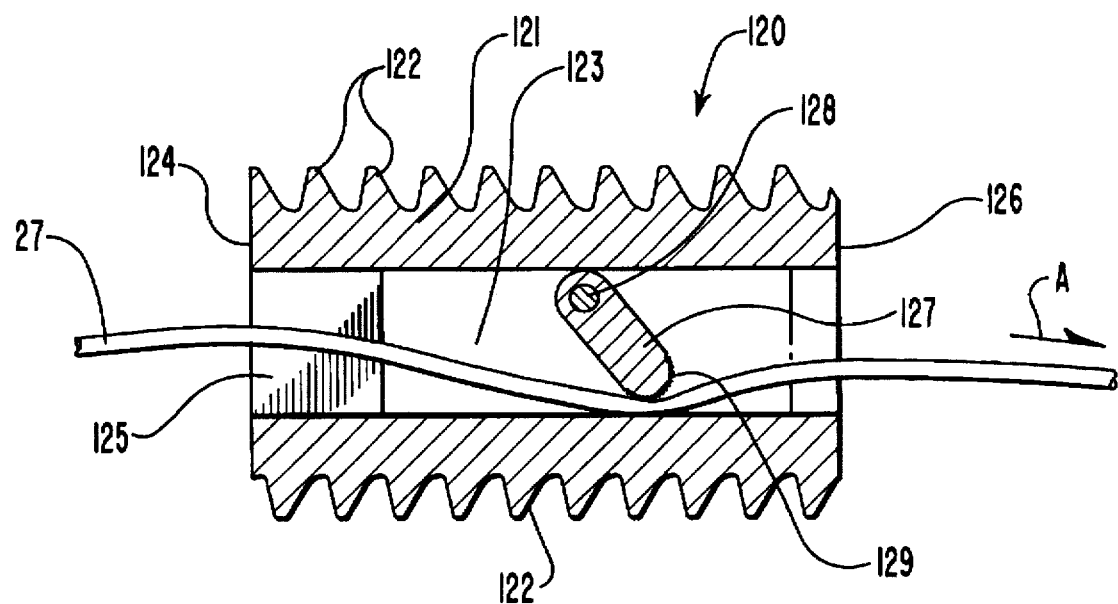
FIG. 21 is a side elevation sectional view of a fourth embodiment of a bone anchor of the invention, showing a body with a center longitudinal cavity wherein a cam is pivotally mounted to swing across the cavity to engage, with a serrated end, a suture fitted therethrough.
Figure 22:
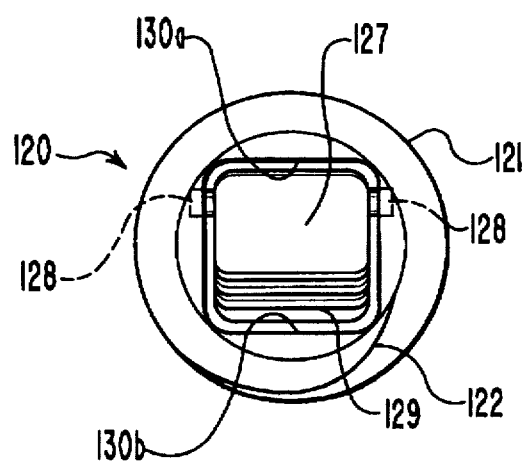
FIG. 22 is a top end view of the bone anchor of FIG. 21, showing the center cavity cross section with the cam pivotally mounted therein.

A fourth embodiment of a bone anchor 120, hereinafter referred to as anchor 120, is shown in FIGS. 21 and 22. Anchor 120 is like anchors 80 and 100 and preferably has a cylindrical body 121 and is thread at 122 for turning into a ligament tunnel section, as described for anchor 80 in FIGS. 6, 7 an 8. A longitudinal cavity is formed through anchor body 121 that exits an anchor distal end 124 wherein are formed sides 125 for receiving a turning tool, like the turning tool 21 of FIG. 6, fitted therein. From the sides 125 the anchor body is stepped into a longitudinal cavity 123 that, like longitudinal cavity 103, has a rectangular cross section or the like, with flat parallel top and bottom walls 130a and 130b, to exit the anchor proximal end 126. A cam 127 is pivotally mounted at 128 to pivot across the cavity 123, bringing serrations 129 formed along a cam lower end into engagement with a section of a suture or sutures 27 fitted through the anchor 120. Accordingly, the cam is moved response to suture 27 travel, arrow A, through the anchor 120, with the cam 127 pivoting towards the anchor proximal end 126 when the suture is pulled out of the anchor proximal end. The cam 127 pivots towards the anchor distal end 124 when a tension is exerted on the suture or sutures 27 to pull them back through the anchor distal end. Accordingly a tension applied to the suture opposite to arrow A, pulls the cam 127 end serrations 129 into engagement with the suture or sutures, crushing the suture against the bottom wall 130b prohibiting further suture travel back through the anchor distal end, locking the sutures in place.

Figure 23:
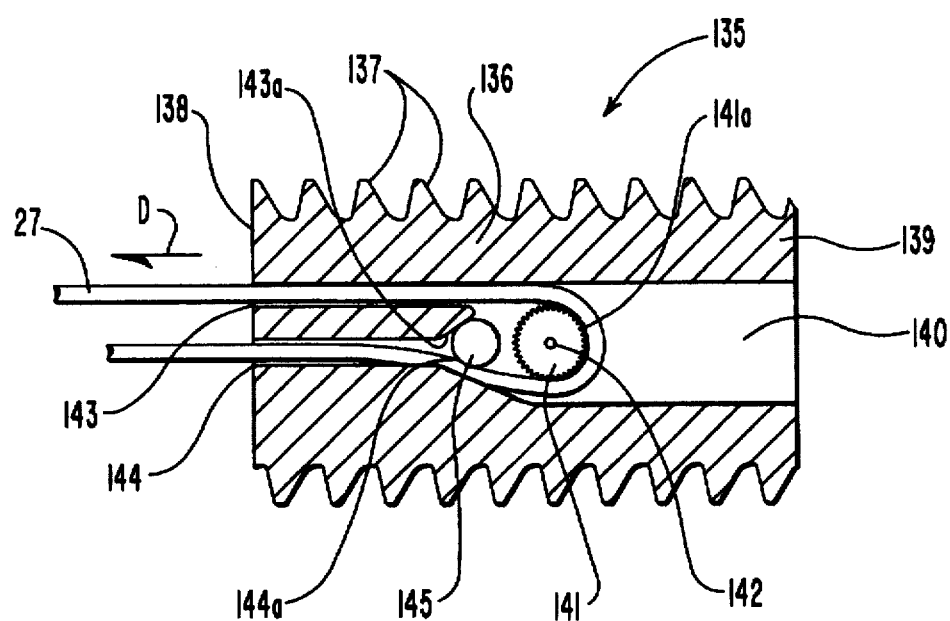
FIG. 23 is a side elevation longitudinal section of a fifth embodiment of a bone anchor of the invention that is a turn back locking device with a suture turned back upon itself after passage around a fixed or rotating pulley which may be geared and across a lock ball.

FIG. 23 shows still another or fifth embodiment of an anchor 135 of the invention that also includes a cylindrical body 136 with teeth 137 formed around and along the cylindrical body outer surface. A forward longitudinal cavity 140 is provided in the body proximal end wherein is arranged a gear 141 which may be fixed or rotating or without teeth that is mounted to an axle 142 that is journaled across the proximal cavity and may be arranged to turn in one direction, such as a clockwise direction, only. In this embodiment, a pair of parallel longitudinal holes 143 and 144 are shown formed into the body distal end that enter the forward proximal cavity 140, the holes 143 and 144 may be sloped, respectively, at 143a and 144a so as to provide a seat for a lock ball lock 145. The suture 27, as shown, is fitted through the first hole 143 and passes around the fixed or rotating pulley 141 which may have serrations 141a of the pulley 141 and back across the ball 145, that can include surface serrations thereover to increase friction and out through the passage 144. The pulley 141 may be free wheeling with suture locking provided by the action of the lock ball 145 crushing it against the seat. Alternatively, the pulley 141 can be arranged to turn only in one direction, such as a clockwise direction only, with the teeth or serrations 141a prohibiting slippage of the suture back through first hole 143. So arranged, suture locking will be provided by the operation of lock ball 145 and pulley 141. It should, however, be understood that the lock ball and seat or the gear arranged to turn in one direction only each can alone function to lock the suture 27 in anchor 135, as shown. The seat surface for lock ball 145 is provided by the sloping surfaces 143a and 144a, the lock ball to be pulled thereagainst when a force, illustrated by arrow D, is exerted on the suture 27 be pulled out, from the passage 144. The anchor 135 functioning as a turn back anchor. Utilizing the anchor 135, it is possible to seat the suture without the necessity of forming a hole through the bone cortex surface of the tunnel wherein the anchor is seated. Anchor 135 therefore provides for fitting into a blind tunnel and for pulling a suture, through the anchor from the single tunnel entrance. To pull into and secure a ligament graft, or the like, in that blind tunnel. Pulling, the lock ball 145 is pulled against the seat formed by surfaces 143a and 144a crushing the suture surface therebetween. Tension on the lock ball to move the lock ball into suture crushing attitude, is further maintained by the gear 141 when it is arranged to turn, as shown, in a clockwise direction only, further prohibiting the suture from pulling the lock ball 145 off of its seat at 143a and 144a. A one-way pulling of the suture that turns back upon itself is thereby provided.

Figure 25:
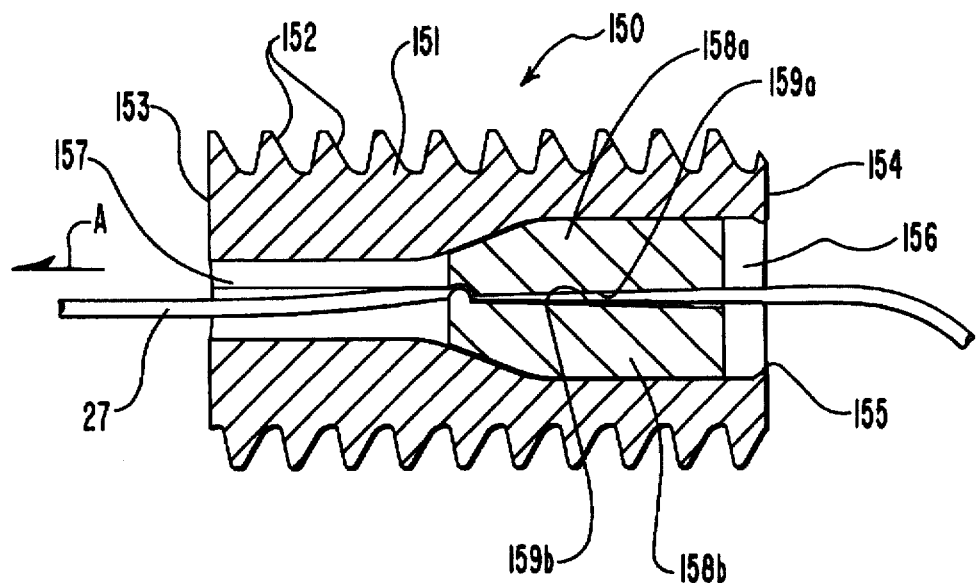
FIG. 25 is a side elevation longitudinal section of a sixth embodiment of the invention showing a suture being crushed between opposing faces of plug halves maintained in a body smooth walled center longitudinal cavity.
Figure 26:
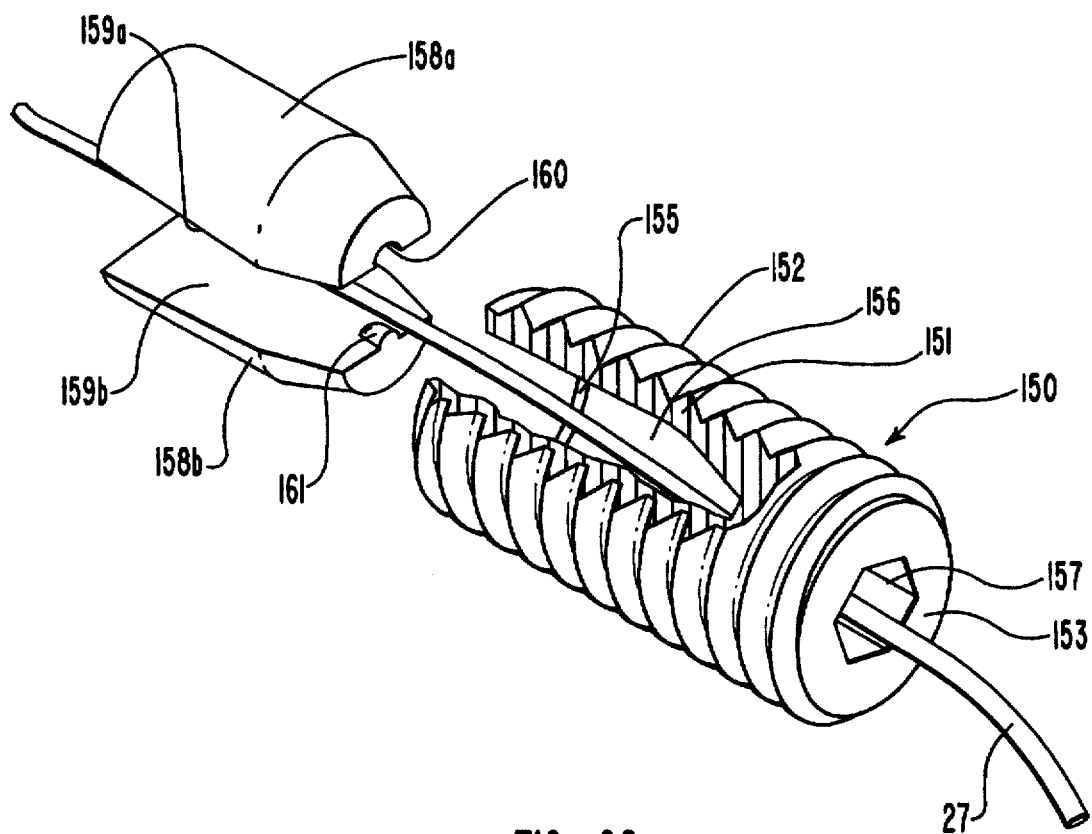
FIG. 26 is an enlarged exploded perspective view of the plug halves of FIG. 25 pulled out of the body center longitudinal cavity wherefrom a section has been removed, and showing the plug halves separated freeing the suture therebetween.

A sixth embodiment of an anchor 150 of the invention is shown in FIGS. 25 and 26. Like the earlier described anchors, anchor 150 includes a cylindrical body 151 with threads 152 formed around its outer surface and along the length thereof. The threads 152, it should be understood, are preferably the same type threads as those described above for the first through the fifth embodiments. Anchor 135, as shown, includes a proximal cavity 156 formed into its proximal end 154 that is inturned at 155 and slopes inwardly to a mid section of the anchor body, that intersects with a distal passage 157 with uniform diameter that extends longitudinally from the anchor distal end 153. To provide suture 27 locking within the anchor, a pair of collet halves 158a and 158b, that are shown best in FIG. 26, are provided. The collet halves have opposing flat surfaces 159a and 159b respectively wherebetween the suture 27 is fitted. The halves each have a flat arcuate shaped flat forward end that, when fitted together form, a flat circle as the collect proximal end. The collet half 158a includes a depression 160 formed therein, with collet 159b having a dent, or raised section, 161 formed therein that is to fit within the depression 160 for aligning the collet halves 158a and 158b. As shown, from the flat proximal ends of the joined, as shown in FIG. 25, collet half, the bodies slope outwardly forming a cone shaped forward section that intersects a cylindrical body extending the length thereof. With the collet halves maintained together, suture 27 is fitted longitudinally therebetween and extends through the passage 157 and cavity 156. The collet halves are retained within the cavity 156 the inturned end section 155. So arranged, the suture can be pulled from the passage 157, out the cavity 156. Should, however, the suture 27 be pulled, as indicated by arrow A, the suture will bind between the collet halves opposing surfaces 159a and 159b, pulling them to the attitude shown in FIG. 25. So arranged, the suture 27 will be crushed and held tightly between the opposing faces 159a and 159b locking suture in place.

The above fifth and sixth embodiments of anchors 135 and 150, like the earlier described first through fourth embodiments, provide for locking a suture 27 as has been pulled therethrough against being pulled back through an anchor body, as described. The anchors, one through four and six are suitable for pulling a suture through the respective anchor, through tunnel ends. Whereas, the anchor of the fifth embodiment 135 can be used for in a blind tunnel procedure, or the like, with the suture 27 as has been attached to a graft form the same tunnel end that the graft is being pulled through. This arrangement allows for use of the anchor 135 in a closed or blind tunnel having a single open tunnel end only.

Figure 7:
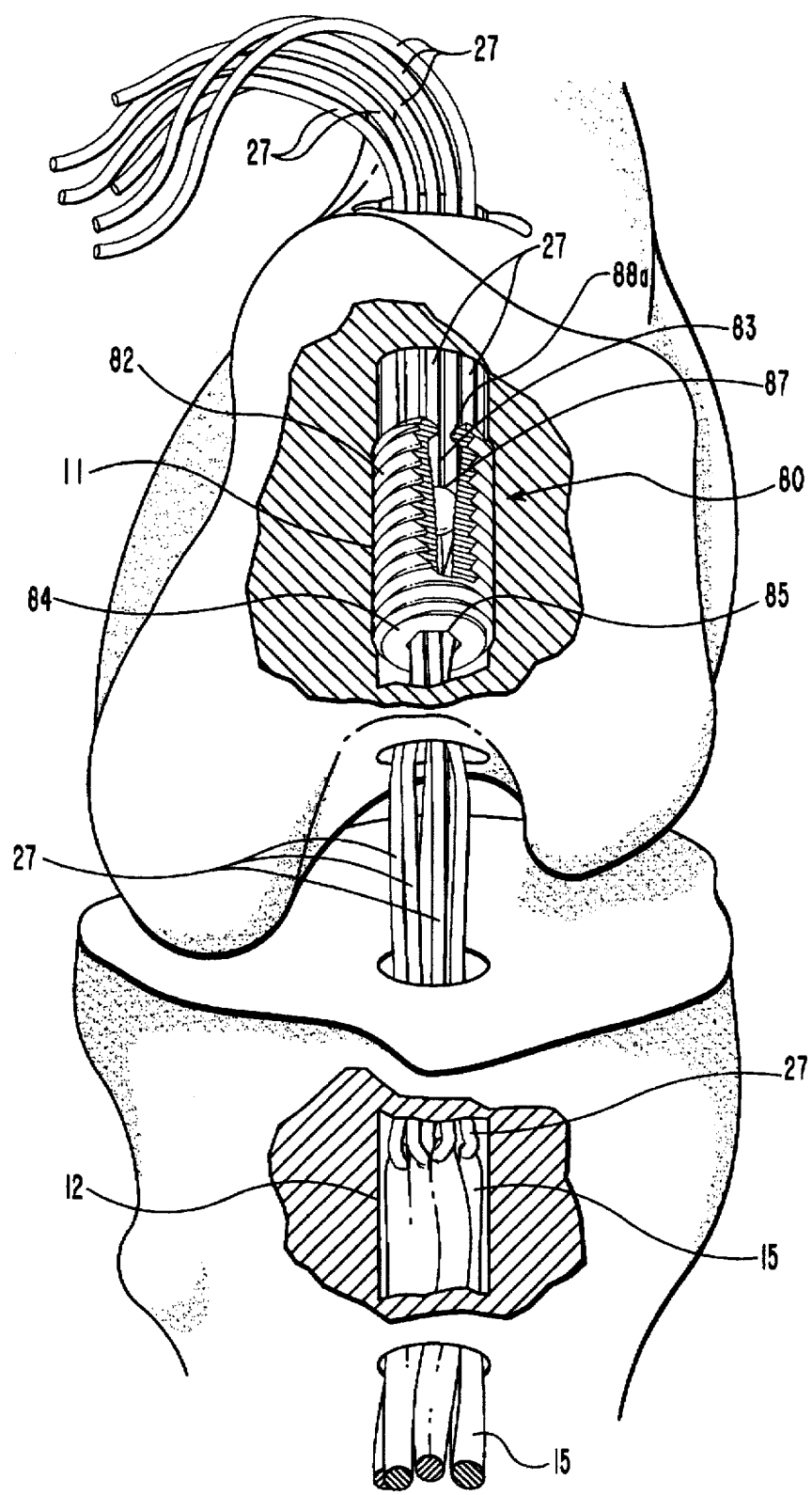
FIG. 7 is a front view of the knee of FIG. 6, with sections removed from the femur and tibia to expose the cylindrical body wherefrom longitudinal section has been removed, and showing the sutures as having been pulled through the invention from distal to proximal ends, pulling the end of the ligament graft that is shown as a soft tissue into the tibial tunnel section.

In practice, a bone anchor 10, 40 and 80 and 100, 120, 135 and 150 of the invention may be used for mounting a femoral end of a ligament graft 14 in an anterior cruciate ligament, with the installation of anchor 80 illustrated in FIGS. 6 through 8, and showing anchor 40 being released in FIG. 17. It should, however, be understood, as set out above, that the bone anchors of the invention are not limited for use in cruciate ligament repair replacement procedure only and may be used for securing a suture to a graft end under tension in a prepared ligament tunnel in procedures involving a patient's shoulder, foot, or the like, and may be for use for mounting a suture alone to a bone mass, within the scope of this disclosure.

FIG. 6 shows the anchor 80 mounted onto an end 22 of turning tool 21 and turned into the femoral tunnel section 11. Which anchor 80 utilization should be taken as being essentially the same for anchors 10, 40 and 100, 120, 135 and 150, except that anchor 135 is suitable for use in a blind tunnel procedure, as provided for within the scope of this disclosure.

FIG. 7 shows the ligament 15 as having been drawn into the tibial tunnel 12 by pulling the sutures 27 through the anchor 80 by a surgeon/operator pulling on the suture 27 ends that extend from the femoral cortex end of the femoral tunnel 11. In which suture travel through anchor 80, the spherical ball 87, as shown, or the plug 30 or 50 of anchors 10 and 40, or the cylindrical roller 107 or cam 127 of anchors 100 and 120, and collet halves 158a and 158b of anchor 150 is displaced in the direction of suture pulling to allow the suture 27 to slide freely therethrough.

FIG. 8 shows the suture 27 as having been pulled through the anchor 80 to where the end of the ligament 15 sewn to the sutures is proximate to or in engagement with the cylinder distal end 84 that is seated within the bone endosteum of the femoral tunnel section 11. So arranged, the graft bone end 16 will have traveled into the tibial tunnel section 12 such that the end 16a thereof is within the tibial tunnel section. Set screw 28, or the like, will have been turned through the tibial and into the bone end 16, mounting the ligament graft tibial in that tibial tunnel section. Pulling of the sutures 27 through all of the anchors 10, 40, 80, 100 and 120, 135, and 150 thereby provide for application of a tensile stress or force into the ligament graft 14. Which applied tension acts also on the spherical ball 87, plugs 30 or 50 at ridges 35 or 46, and cylindrical roller 107, cam 127, locking ball 145, or collet halves 158a and 158b that are thereby drawn such that the opposing movable member and cylindrical body surfaces or opposing surfaces 159a and 159b of the collet halves are urged together, crushing sections of the sutures 27 therebetween, resisting passage of the sutures back through the anchor. The ligament graft 14 is thereby mounted, under tension and required length within the tunnel sections or blind tunnel section, and the sutures 27 can then be cut off.

Distinct from anchor 10, anchor 40, as shown and described above, is arranged to allow for the release of the tension applied to the ligament graft 14 and the release of the sutures 27, allowing them to be pulled through the anchor and into the knee joint. With the anchor 40 in place, as set out above with reference to the discussion of the use of anchor 10, to release the tensioning on the ligament graft 14 applied through sutures 27, flat face 73 of tool 70 is fitted into the femoral tunnel cortex end to engage the top face 63 of the set screw 60 that has been turned into the plug 50 prior to its installation in the patient's knee. The tool 70 is turned until the short posts 74 that extend from flat face 73 align with and travel into holes 64 formed into the set screw top face 63. The tool 70 thereby engages the set screw 60 and, with tool turning, the set screw it turned through the plug 50, as shown in FIG. 12, to where the set screw end 65 engages the wall 48. Whereat, with continued set screw 60 turning, the plug 50 ridges 56 are urged away from the cylindrical body ridges 46 releasing the crushing force applied to the sutures 27. The sutures are thereby released and can travel through the anchor 40 and into the knee joint. Tension on the ligament graft 14 is thereby released and the graft can be removed from the tunnel sections and the anchor turned out of the femoral tunnel utilizing tool 21. Similarly, should it be desired to displace the spherical ball 87, cylindrical roller 107, cam 127, lock ball 145 or collet halves 158a and 159b to release the suture 27 a rod, not shown, can be fitted through the anchor distal end 84, 104, 124, 138 or 153, through openings 85, 105, 125, 144 or 157, to disengage the movable member so as to release suture 27 allowing removal thereof.

While preferred embodiments of our invention in bone anchors and methods for their use have been shown and described herein, it should be understood that the present disclosure is made by way of example only and that variations and changes and uses other than those specifically described or referred to are possible without departing from the subject matter and reasonable equivalency thereof coming within the scope of the following claims, which claims we regard as our invention.

We claim:

1. A bone anchor comprising a body that includes means for securing said body in a tunnel section formed in a bone mass and includes an axial opening with an end of said opening formed to receive an insertion tool and is configured to receive a clamping means fitted therein; a clamping means formed to fit within and be axially movable within said body axial opening so as to move a clamping surface or surfaces towards a surface of said body axial opening and said clamping means is to engage a surface of a suture or shaft means fitted in a said axial opening to clamp said suture or shaft means surface against said surface of said body axial opening; means for maintaining said clamping means to be movable in said axial opening; and at least one said suture or shaft means for fitting in said body to pass between said surface or surfaces of said clamping means and said surface of said body axial opening.

2. A bone anchor as recited in claim 1, further including one or both ends of the body axial opening is sided to receive a like sided end of a turning tool means for turning said body into a bone tunnel.

3. A bone anchor as recited in claim 1, wherein a concave cup means is formed at the junction of the axial opening and mid section, and the axial opening tapers outwardly therefrom to have an elongated arcuate shape at the body proximal end; and the clamping means is a spherical ball of lesser diameter than the distance across said axial opening.

4. A bone anchor as recited in claim 3, wherein the suture or shaft means is fitted through the body, from the distal end, through the turning tool portion of the axial opening, between the axial opening surface and the surface of the spherical ball and out of said axial opening proximal end; and the edge of said axial opening at the body proximal end is formed to provide a lesser distance across the flattened ellipse than the diameter of said spherical ball to function as the means for containing said spherical ball.

5. A bone anchor as recited in claim 3, further including scoring the spherical ball surface.

6. A bone anchor as recited in claim 1, further including a plurality of equally spaced apart radial holes formed in the body distal end around and parallel to the axial opening and extending through a dividing wall formed across said body; and one each of a plurality of suture or shaft means is fitted through each said radial hole, extending through said body.

7. A bone anchor as recited in claim 6, wherein the surface of the body axial opening, adjacent to the dividing wall includes at least one ridge formed therearound; and the clamping means is a plug formed to fit through the body proximal end and into said axial opening, said plug having a body with at least one ridge formed around its outer surface that is shaped to oppose a surface of said axial opening ridge, and said plug body includes a flat disk head end wherein a plurality of spaced radial holes are formed, each to receive one of the plurality of suture or shaft means passed through the body radial holes.

8. A bone anchor as recited in claim 7, further including a center longitudinal passage formed through the plug; and the means for containing the plug in the axial opening is an inturning of the axial opening edge at the body proximal end.

9. A bone anchor as recited in claim 8, wherein the plug center longitudinal passage is threaded to receive a set screw turned therein from the body proximal end, through the plug longitudinal passage and into engagement with the dividing wall to move said plug away from said dividing wall so as to release a clamping action of the plug ridge applied to the suture or shaft means surface that clamps against the axial opening ridge.

10. A bone anchor as recited in claim 9, wherein the set screw includes at least one opening formed into its proximal end for receiving an end of a turning tool means fitted therein.

11. A bone anchor as recited in claim 1, wherein the axial opening has a sided cross section; the clamping means has a round cross section and includes axles extending from its opposite ends that are journaled in longitudinal parallel tracks that are formed in opposing parallel side walls of said axial opening; and means for maintaining said clamping means within said axial opening.

12. A bone anchor as recited in claim 11, wherein the axial opening is serrated across its top and bottom surfaces and its proximal end is inturned along parallel sides to form an opening of lesser diameter than the width of the clamping means; and said clamping means is scored over its outer surface.

13. A bone anchor as recited in claim 1, wherein the axial opening has a sided cross section; and the clamping means is a cam formed to fit in and extend across said axial opening and is axially coupled at one end across said axial opening to swing across said axial opening.

14. A bone anchor as recited in claim 13, wherein the cam end opposite to its pivot end includes slot means formed thereacross for engaging a suture or shaft means.

15. A bone anchor as recited in claim 1, wherein the tunnel section includes a longitudinal cavity formed in the body proximal end to a mid-section thereof and including a pair of longitudinal first and second passages extending from the body distal end to intersect said longitudinal cavity; with the junction of one of said first or second passages and said longitudinal cavity formed into a seat; a lock ball arranged for fitting in said seat is provided as the movable clamping means; and a pulley means is journaled across said longitudinal cavity to receive the suture or shaft means passed through the first or second passages and across the seat to exit the other first or second passage.

16. A bone anchor as recited in claim 15, wherein the pulley means is arranged to turn only in the direction of travel of the suture or shaft means through the body.

17. A bone anchor as recited in claim 1, wherein the tunnel section is formed through the body from a greater diameter uniform cross section portion from the body proximal end, sloping uniformly inwardly at the body mid-section, and intersecting a lesser diameter uniform cross section portion that exits the body distal end, with means for reducing the diameter of said greater diameter portion of said body proximal end; and the clamping means is a pair of collet halves having flat opposing faces with inwardly sloping forward ends to fit into said uniformly sloping tunnel section, and rear portions to fit within said tunnel section greater diameter portion, to slide back and forth therein, with the suture or shaft means to fit between said collet halves opposing faces.

18. A bone anchor as recited in claim 17, further including, the collet halves inwardly sloping forward ends end in flat faces, and including a depression formed in one collet half, adjacent to said flat face, with a detent formed in the other collet half, adjacent to said flat face, to receive said detent fitted therein; and the means for reducing the diameter of the greater diameter portion of the body proximal lip is provided by inturning the edge of said greater diameter portion at the body proximal end.

\* \* \* \* \*